US012564424B2

(12) United States Patent
Kadlub et al.

(10) Patent No.: US 12,564,424 B2
(45) Date of Patent: Mar. 3, 2026

(54) ACTIVATION TOOL FOR A BONE EXPANSION APPARATUS

(71) Applicants: ECOLE NATIONALE SUPERIEURE DE TECHNIQUES AVANCEES, Palaiseau (FR); ASSISTANCE PUBLIQUE HOPITAUX DE PARIS, Paris (FR)

(72) Inventors: Natacha Kadlub, Paris (FR); Jean Boisson, Paris (FR); Jeremy Dallard, Joinville-le-Pont (FR); Emilie Su, Montreuil (FR)

(73) Assignees: ECOLE NATIONALE SUPERIEURE DE TECHNIQUES AVANCEES, Palaiseau (FR); ASSISTANCE PUBLIQUE HOPITAUX DE PARIS, Paris (FR)

( * ) Notice: Subject to any disclaimer, the term of this patent is extended or adjusted under 35 U.S.C. 154(b) by 447 days.

(21) Appl. No.: 18/260,068

(22) PCT Filed: Dec. 23, 2021

(86) PCT No.: PCT/EP2021/087472
§ 371 (c)(1),
(2) Date: Dec. 7, 2023

(87) PCT Pub. No.: WO2022/144296
PCT Pub. Date: Jul. 7, 2022

(65) Prior Publication Data
US 2024/0216017 A1     Jul. 4, 2024

(30) Foreign Application Priority Data
Dec. 30, 2020   (FR) ...................................... 2014283

(51) Int. Cl.
| | | |
|---|---|---|
| A61B 17/66 | (2006.01) | |
| A61B 17/04 | (2006.01) | |
| A61B 17/68 | (2006.01) | |

(52) U.S. Cl.
CPC ............ *A61B 17/663* (2013.01); *A61B 17/68* (2013.01); *A61B 2017/0477* (2013.01); *A61B 2017/681* (2013.01)

(58) Field of Classification Search
CPC .............................. A61B 17/663; A61B 17/68
See application file for complete search history.

(56) References Cited

U.S. PATENT DOCUMENTS

| | | | | |
|---|---|---|---|---|
| 6,355,036 | B1 * | 3/2002 | Nakajima | .............. A61B 17/66 606/57 |
| 12,220,154 | B2 * | 2/2025 | Qi | ...................... A61B 17/6475 |

(Continued)

FOREIGN PATENT DOCUMENTS

| | | |
|---|---|---|
| CN | 111920502 A | 11/2020 |
| FR | 2906453 A1 | 4/2008 |

(Continued)

OTHER PUBLICATIONS

Japanese Office Action issued May 20, 2025, in Japanese Patent Application No. 2023-540568, 6 pages. shaft (9) and the second shaft (15) exhibit the same rotational speed, and is configured to angularly (Continued)

*Primary Examiner* — Christian A Sevilla
(74) *Attorney, Agent, or Firm* — Vorys, Sater, Seymour and Pease LLP; Rex W. Miller, II

(57) ABSTRACT

The invention relates to an activation tool (3) comprising in particular:
  a coupling device (17) interposed between a first shaft (9) and a second shaft (15), which is configured to couple the first shaft (9) and the second shaft (15) in a first mode, referred to as the activation mode, when the first (Continued)

decouple the first shaft (9) and the second shaft (15) in a second mode, referred to as the failure mode, when a rotational speed of the second shaft (15) is higher than the rotational speed of the first shaft (9), means (19) for detecting the switch from the first mode to the second mode.

The invention also relates to a distraction assembly (1) having an activation tool (3) of the above-mentioned type, and a plate distractor (5).

10 Claims, 3 Drawing Sheets

(56) References Cited

U.S. PATENT DOCUMENTS

2002/0035368 A1* 3/2002 Schumacher ........ A61B 17/663
606/86 R

2007/0173837 A1* 7/2007 Chan ..................... A61B 17/66
606/63
2015/0272644 A1* 10/2015 Noon .................... A61B 17/66
606/90

FOREIGN PATENT DOCUMENTS

| JP | 2012157377 A | 8/2012 |
|----|--------------|--------|
| WO | 2008003952 A1 | 1/2008 |
| WO | 2018165243 A1 | 9/2018 |
| WO | 2020069627 A1 | 4/2020 |

OTHER PUBLICATIONS

International Search Report and Written Opinion issued Feb. 4, 2022 for PCT/EP2021/087472, 11 pages.

* cited by examiner

[Fig. 1]
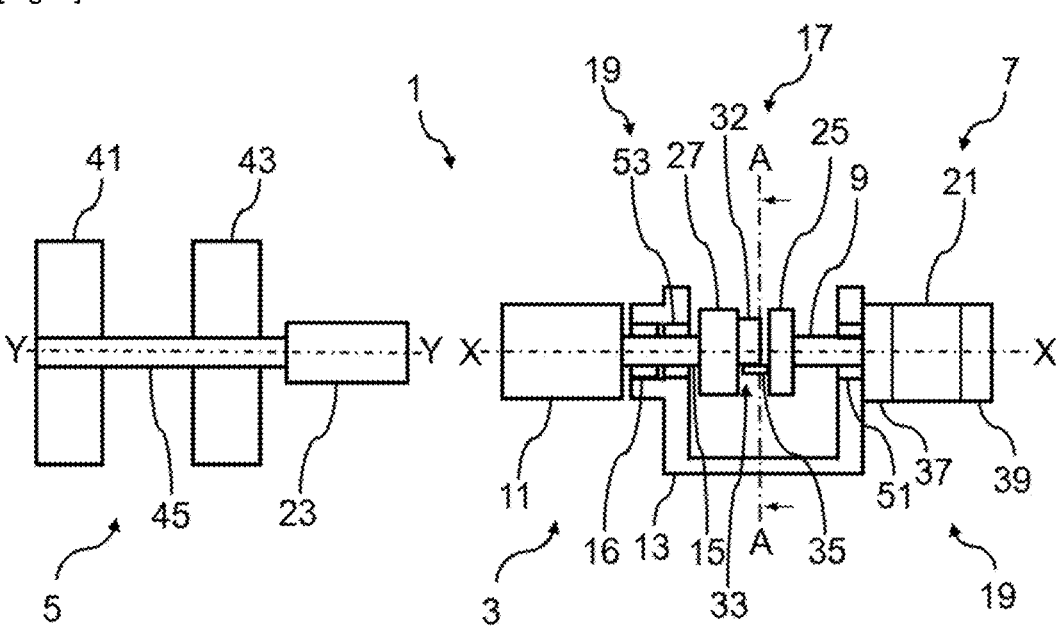
[Fig. 2]
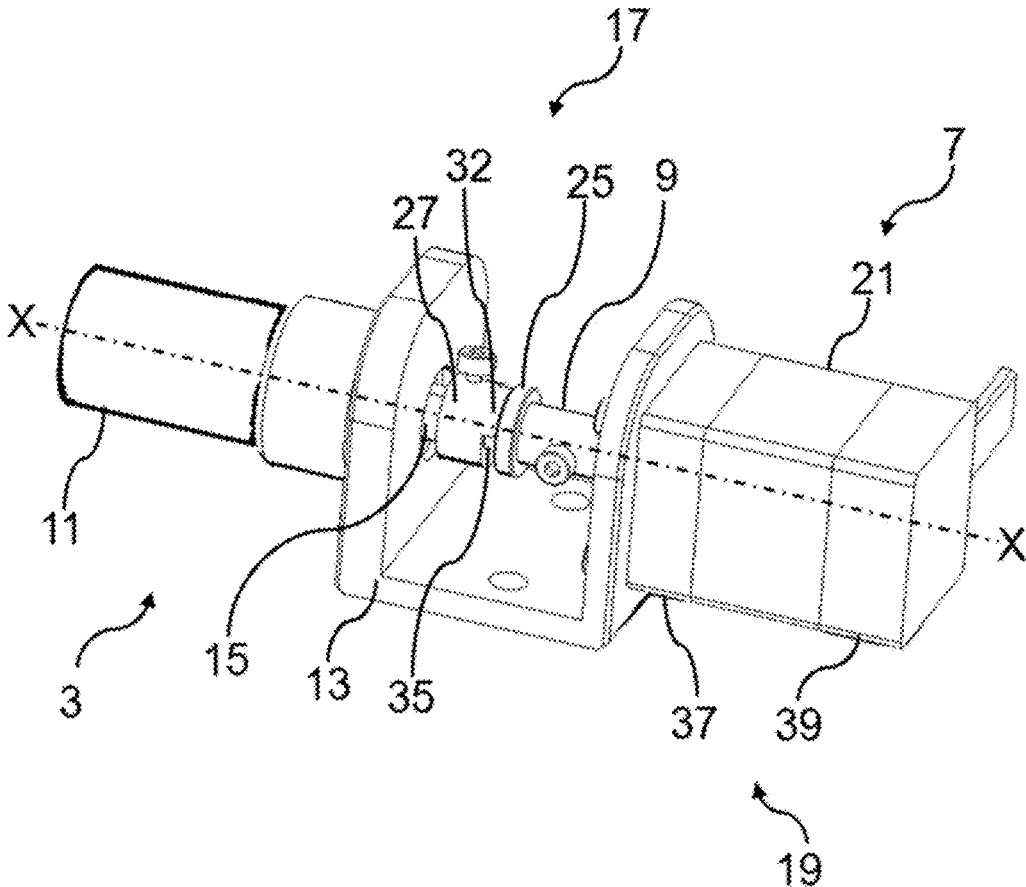

[Fig. 3]
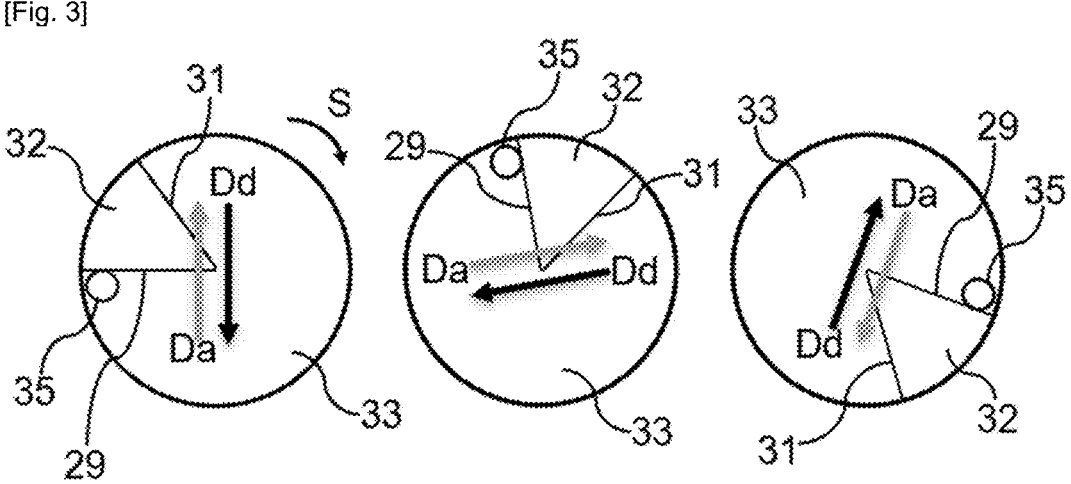
[Fig. 4]
- 4a -          - 4b -          - 4c -
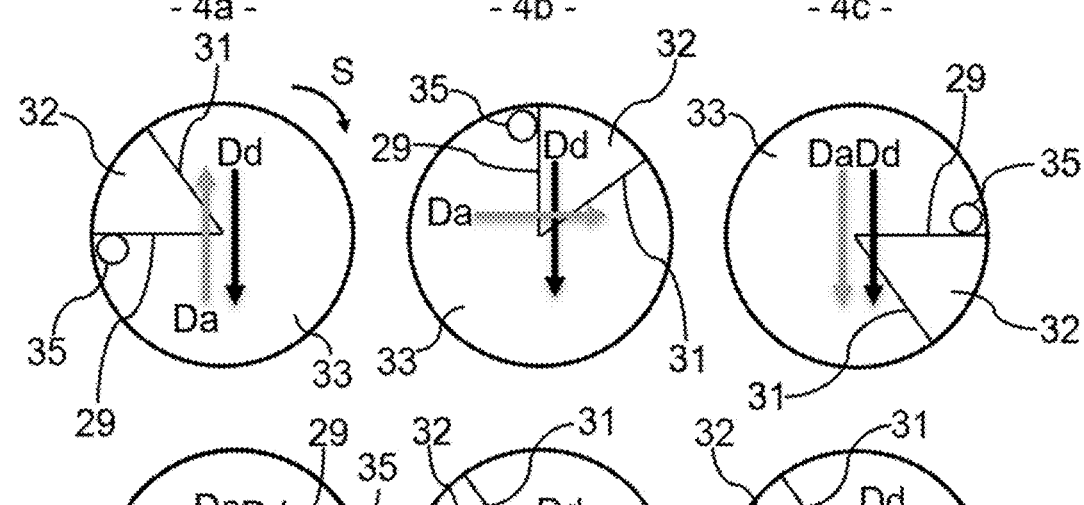
- 4d -          - 4e -          - 4f -
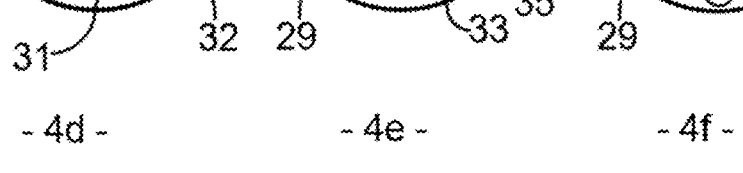

[Fig. 5]
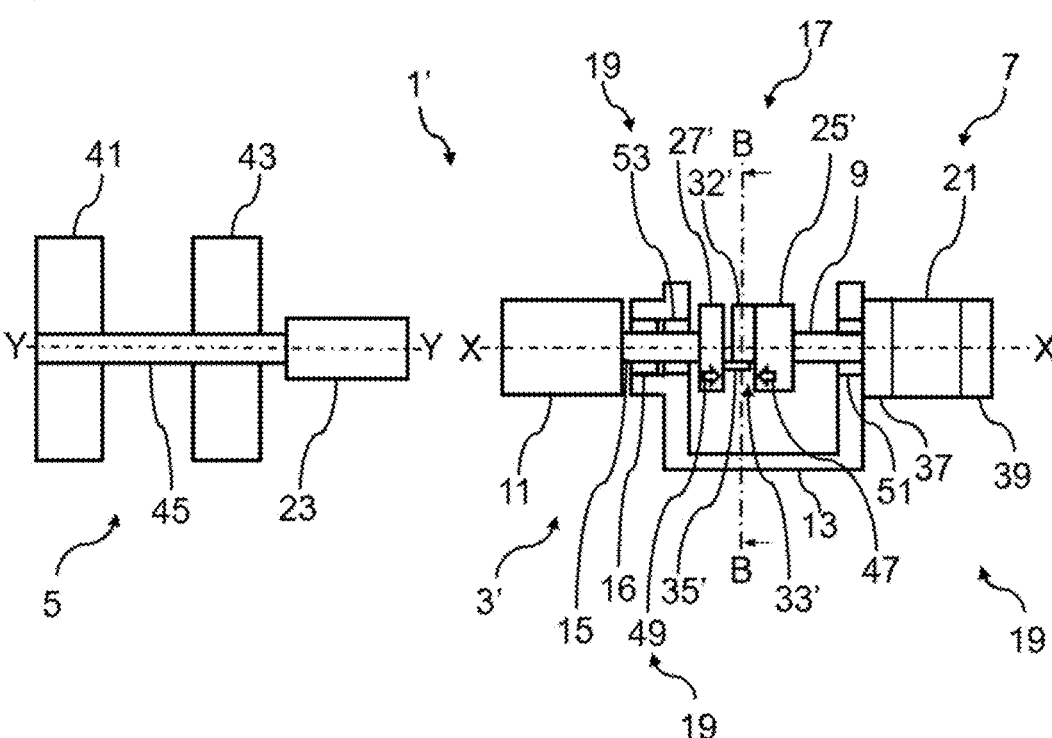
[Fig. 6]
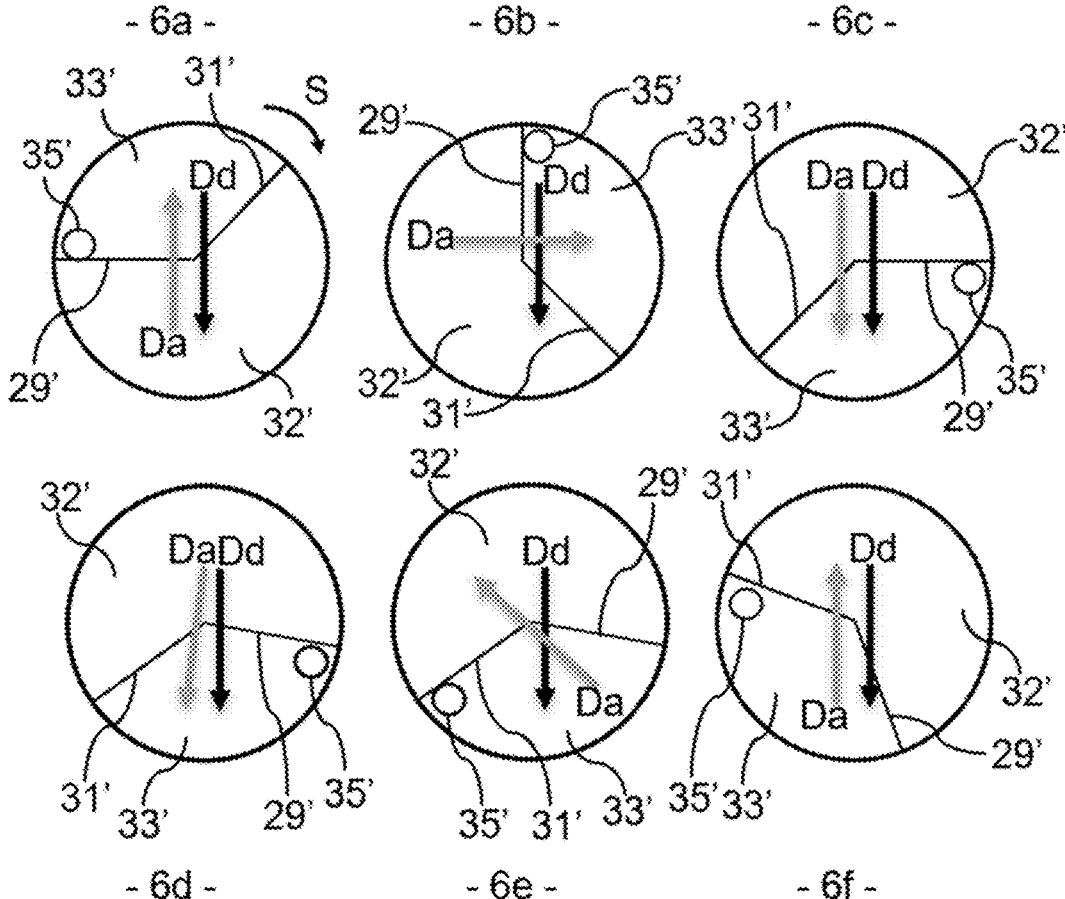

ACTIVATION TOOL FOR A BONE EXPANSION APPARATUS

The invention relates to the field of bone expansion apparatus such as, for example, a plate distractor.

The state of the art, in particular in document WO 2017/097998 A1, already describes a plate distractor designed to perform maxillofacial distraction. Such a plate distractor is attached to one side of a bone or to the side of adjacent bones of a subject and comprises a rotating magnet near one end of the plate distractor.

This magnet is rotated, using an external activation tool also bearing a magnet, about an rotation axis coinciding with the rotation axis of the distractor magnet, to perform bone distraction. To do this, the rotation of the distractor magnet causes the distractor plates to separate by means of a worm screw mechanism. The worm screw converts the rotational movement of the distractor magnet into a translational movement of one distractor plate relative to the other plate, causing the plates to separate.

The bone distraction assembly described in this document comprises an activation tool external to the distractor, the rotation of said tool causing the rotation of the plate distractor magnet by magnetic coupling. In this case, the activation magnetic element and the remote magnetic element supported by the bone expansion apparatus simply have to be placed opposite each other. Thus, with such a coaxial configuration, rotation of the activation magnetic element about itself about an activation rotation axis causes the remote magnetic element supported by the bone expansion apparatus to rotate about itself about a distraction axis.

In this coaxial configuration, the rotation axis of the remote magnetic element, also called distraction axis, coincides with the rotation axis of the magnetic element of the activation tool. Thus, the rotation of the remote magnetic element supported by the bone expansion apparatus is obtained via the coaxial interaction between the magnetic element of the activation tool and the remote magnetic element supported by the bone expansion apparatus, without generating a tearing force on the bone expansion apparatus along a direction perpendicular to the distraction axis. This is particularly advantageous when the bone expansion apparatus is a plate distractor. Such a plate distractor is in fact often used on very young children and is, for example, attached to the bones using short screws, for example 5 mm long, or even plastic resorbable screws. The plate distractor is removed by tearing. Thus, the attachment of the plate distractor on the bones is relatively fragile and the adjustment of the spacing between the attachment plates of the plate distractor must not generate mechanical stresses likely to cause premature tearing. The intensity of the mechanical stresses likely to be exerted on the attachment of the plates to the bones must therefore remain as low as possible so that the plate distractor can be operated in complete safety.

Due to these low mechanical stresses, the remote magnetic element can be blocked in rotation. However, this activation tool is used manually and is unable to easily detect a failure of the plate distractor.

Document WO 2008/003952 A1 also describes a distractor device, preferably a plate distractor, comprising a magnetic element that can be rotated by means of an external magnetic actuator.

The invention aims in particular to simplify the detection of a failure in the operation of a bone expansion apparatus, preferably a plate distractor.

The invention therefore relates to an activation tool for a bone expansion apparatus, preferably for a plate distractor, characterised in that the activation tool comprises:

a drive member provided with a drive output, a first shaft configured to be driven in rotation about a rotation axis via the drive output, an activation magnetic element, the activation magnetic element being configured to interact, preferably coaxially, with a remote magnetic element supported by the bone expansion apparatus, a second shaft, arranged coaxially to the first shaft, the second shaft supporting the activation magnetic element, a coupling device interposed between the first shaft and the second shaft, which is configured to couple the first shaft and the second shaft in a first mode, referred to as the activation mode, when the first shaft and the second shaft exhibit the same rotational speed, and is configured to angularly decouple the first shaft and the second shaft in a second mode, referred to as the failure mode, when a rotational speed of the second shaft is higher than the rotational speed of the first shaft, means for detecting the switch from the first mode to the second mode.

Due to the coupling device provided in the activation tool, it is easy to detect when the rotation of the remote magnetic element is blocked, for example without the need for a magnetic field sensor detecting the angular position of the remote magnetic element. Thus, detection of the switch from the first mode to the second mode, which corresponds to the angular decoupling of the first shaft and of the second shaft, makes it easy to detect a failure of the rotation of the remote magnetic element. Consequently, an activation failure can be easily detected. For example, there is no need to check the rotation of the remote magnetic element using external sensors which must be positioned correctly with respect to the remote magnetic element.

According to other optional characteristics of the activation tool taken alone or in combination:

The drive member comprises an electric motor.

The activation magnetic element is a permanent magnet magnetised along a direction perpendicular to the rotation axis, preferably with axial symmetry relative to the rotation axis.

The second shaft axially supports the activation magnetic element. Thus, the rotation of the second shaft causes the magnetic element to rotate about itself about the rotation axis, the coaxial interaction with the remote magnetic element being optimum in this case.

The coupling device comprises a first coupling member supported by the first shaft, and a second coupling member supported by the second shaft, one selected from the first coupling member and the second coupling member comprising a first angular stop and a second angular stop, the first angular stop and the second angular stop being angularly offset and delimiting between them an angular housing extending over an angle of at least 90° about the rotation axis, the other selected from the first coupling member and the second coupling member comprising a projecting element, the projecting element being engaged in the angular housing such that the second shaft pivots freely about the rotation axis between a first angular position in which the projecting element is in contact with the first angular stop and a second angular position in which the projecting element is in contact with the second angular stop. Thus, the coupling device is particularly simple to produce.

The angle between the first angular position and the second angular position is at least 65°, preferably at least 90°, more preferably at least 180°.

The detection means detect the pivoting of the second shaft out of the first angular position when the first shaft is driven in rotation in a first direction of rotation, and the pivoting of the second shaft out of the second angular position when the first shaft is driven in rotation in a second direction of rotation opposite to the first direction of rotation.

The projecting element is a pin or an angular sector consisting of a disc portion.

The first angular stop and the second angular stop form the angular extremities of an angular sector consisting of a disc portion.

The angular housing extends over an angle of between 90° and 300° about the rotation axis, preferably equal to 295°. Thus, the angular extent of the angular housing is large enough to allow the switch from the first mode to the second mode to be detected easily, and therefore to allow blocking of the remote magnetic element to be detected.

The angular housing extends over an angle of between 90° and 170° about the rotation axis. Thus, the oscillations of the activation magnetic element decrease when it is angularly decoupled from the drive output due to a failure of the rotation of the remote magnetic element. When switching from the first mode to the second mode, the second shaft is in fact angularly decoupled from the first shaft. The projecting element and one of the two angular stops are then no longer in contact with each other, then the projecting element and the other of the two angular stops come into contact angularly, the inertia of the first shaft providing in this case a damping function.

The detection means comprise a visual indicator of the angular position of the first shaft and a visual indicator of the angular position of the second shaft. Thus, the user can easily detect the switch from the first mode in which the visual indicators do not move relative to each other to the second mode in which the visual indicators move relative to each other.

The detection means comprise a first sensor of the angular position of the first shaft and a second sensor of the angular position of the second shaft. Preferably, the detection means comprise a storage memory configured to store the angular position data of the first shaft and of the second shaft. Thus, a practitioner can read these data subsequently, for example every week.

The detection means comprise a torque sensor configured to measure the torque exerted by the electric motor and/or a current sensor configured to measure the current consumed by the electric motor. Thus, a very simple means is available to allow the switch from the first mode to the second mode to be detected easily, and therefore to allow blocking of the remote magnetic element to be detected.

The detection means comprise a visual indicator of the switch from the first mode to the second mode. Preferably, the visual indicator of the switch from the first mode to the second mode comprises a green light emitting diode which is lit when the drive is carried out only according to the first mode, and comprises a red light emitting diode which is lit when the drive is carried out with at least a switch from the first mode to the second mode. Thus, when the drive is finished, the user is informed of a correct operation via the green light emitting diode, and is informed of a detective operation via the red light emitting diode.

The detection means comprise an audible indicator, which emits an audible signal when the drive is carried out only according to the first mode. Thus, when the drive is finished, the user is informed of a correct operation via this audible signal.

The rotational speed of the activation magnetic element in the first mode is less than or equal to 30 revolutions per minute, preferably less than or equal to 18 revolutions per minute. Thus, detection by the user of a switch of the activation tool from the first mode, referred to as the activation mode, to the second mode, referred to as the failure mode, is optimum, since the switch is carried out for a duration that is long enough for the user to visually detect a sudden variation in the rotational speed of the activation magnetic element and/or a vibration and/or an audible variation since the electric motor no longer transmits torque to the second shaft in the second mode, referred to as the failure mode. More precisely, the rotational speed is sufficiently low so that, when the remote magnetic element no longer rotates in interaction with the activation magnetic element, the torque exerted by the remote magnetic element on the activation magnetic element generates an increase in the rotational speed of the activation magnetic element, and consequently an increase in the rotational speed of the second shaft. Thus, this generates a loss of contact between the projecting element and one selected from the first angular stop and the second angular stop, depending on the direction of rotation of the electric motor.

The rotational speed of the activation magnetic element is constant in a first mode referred to as the activation mode. Thus, a variation in the speed of the activation magnetic element is easily detected when the activation tool switches to the second mode, referred to as the failure mode.

The drive member, preferably the electric motor, is configured such that the drive output is driven one revolution at a time. Activation of the plate distractor is in fact difficult and must be carried out in steps to avoid excessive stress on the plate distractor. A step means for example that the drive member drives in rotation the drive output and the first shaft over one revolution, then is stopped, the rotation of the drive output and of the first shaft then being stopped. For example, the above-mentioned step is repeated every day.

The activation tool comprises a ball bearing arranged on the second shaft. Thus, the presence of a ball bearing, due to the frictional forces it generates, reduces any oscillations of the activation magnetic element when the activation tool is in the second mode, referred to as the failure mode.

The activation tool comprises a box and the ball bearing is interposed between the box and the second shaft.

The invention also relates to a distraction assembly comprising:

an activation tool of the type described previously, wherein the activation magnetic element is a permanent magnet magnetised along a direction perpendicular to the rotation axis, and a plate distractor, which comprises a first attachment plate and a second attachment plate, a distraction member configured to modify the distance between the first attachment plate and the second attachment plate, and a remote magnetic element consisting of a permanent magnet, configured to drive the distraction member in rotation about itself about a distraction axis, the remote magnetic element being a permanent magnet magnetised along a direction perpendicular to the distraction axis.

According to other optional characteristics of the distraction assembly, taken alone or in combination:

The distraction assembly is such that, when the distraction axis coincides with the rotation axis: in the first mode, the remote magnetic element is driven in rotation by the activation magnetic element; in the second mode, the remote magnetic element drives in rotation the activation magnetic element until their magnetisation directions are parallel.

The distraction member comprises a threaded rod cooperating with a threaded hole in an attachment plate such as the first attachment plate, such that the thread pitch of the threaded rod is between 0.20 and 0.25 mm per revolution, preferably equal to 0.20 mm per revolution. Thus, during the rotation over one revolution of the threaded rod, the distance between the attachment plates is modified by the value corresponding to the thread pitch, the attachment plates moving closer together or farther away from each other depending on the direction of rotation.

BRIEF DESCRIPTION OF THE FIGURES

The invention will be better understood on reading the following description, given solely by way of example and with reference to the accompanying drawings in which:

FIG. 1 is a diagrammatic cross-sectional front view of a distraction assembly comprising an activation tool according to a first embodiment;

FIG. 2 is a diagrammatic perspective view of the activation tool according to the first embodiment;

FIG. 3 is a set of diagrammatic cross-sectional views through the plane A-A of the activation tool according to the first embodiment in a first mode, referred to as the activation mode.

FIG. 4 is a set of diagrammatic cross-sectional views through the plane A-A of the activation tool according to the first embodiment in a second mode, referred to as the failure mode.

FIG. 5 is a diagrammatic cross-sectional front view of a distraction assembly comprising an activation tool according to a second embodiment.

FIG. 6 is a set of diagrammatic cross-sectional views through the plane B-B of the activation tool according to the second embodiment in a second mode, referred to as the failure mode.

DETAILED DESCRIPTION

On all the figures, the same references refer to the same elements. In this detailed description, the following embodiments are examples. Although the description refers to one or more embodiments, this does not mean that the characteristics apply only to a single embodiment. Simple characteristics of different embodiments may also be combined and/or interchanged to provide other embodiments.

In this description, some elements or members are designated by names or expressions, such as for example "first shaft" or "second shaft". In this case, these designations are used to differentiate and name elements or members that are not identical. These designations do not imply a priority or a hierarchy of one element (or member) over another and it is quite possible to interchange such names without departing from the scope of this description. Similarly, these designations do not imply an order in time for example to appreciate such or such criteria.

FIG. 1 is a diagrammatic representation of a distraction assembly according to a first embodiment, designated by the general reference 1.

The distraction assembly 1 comprises an activation tool 3 and a plate distractor 5.

The activation tool 3 comprises: a drive member 7 provided with a drive output, a first shaft 9 configured to be driven in rotation about an rotation axis XX by the drive output, and an activation magnetic element 11.

The activation tool 3 also comprises a second shaft 15, arranged coaxially to the first shaft 9, the second shaft 15 supporting the activation magnetic element 11. A ball bearing 16 is arranged on the second shaft 15. More precisely, the activation tool 3 comprises a box 13 and the ball bearing 16 is interposed between the box 13 and the second shaft 15. In addition, the box 13 supports the driver member 7.

The activation tool 3 further comprises a coupling device 17 interposed between the first shaft 9 and the second shaft 15, which is configured to couple the first shaft 9 and the second shaft 15 in a first mode, referred to as the activation mode, when the first shaft 9 and the second shaft 15 exhibit the same rotational speed, and is configured to angularly decouple the first shaft 9 and the second shaft 15 in a second mode, referred to as the failure mode, when a rotational speed of the second shaft 15 is higher than the rotational speed of the first shaft 9. Lastly, the activation tool 3 comprises means 19 for detecting the switch from the first mode to the second mode.

In this example, the drive member 7 comprises an electric motor 21, which drives in rotation the first shaft 9 via the drive output.

The drive member 7, preferably the electric motor 21, is configured such that the drive output is driven one revolution at a time. The drive member 7 drives in rotation the drive output and the first shaft 9 over one revolution, then is stopped, the rotation of the drive output and of the first shaft 9 then being stopped. For example, the above-mentioned step is repeated every day.

The activation magnetic element 11 is supported axially by the second shaft 15. The activation magnetic element 11 is configured to interact, preferably coaxially, with a remote magnetic element 23 supported by the plate distractor 5. In this example, the activation magnetic element 11 is a permanent magnet magnetised along a direction Da perpendicular to the rotation axis XX, preferably with axial symmetry relative to the rotation axis XX. The rotational speed of the activation magnetic element 11 in the first mode is less than or equal to 30 revolutions per minute, preferably less than or equal to 18 revolutions per minute. For example, the rotational speed of the activation magnetic element 11 is constant in the first mode.

The coupling device 17 comprises a first coupling member 25 supported by the first shaft 9, and a second coupling member 27 supported by the second shaft 15. In this example, shown in particular on FIGS. 3 and 4, the second coupling member 27 comprises a first angular stop 29 and a second angular stop 31, the first angular stop 29 and the second angular stop 31 being angularly offset and delimiting between them an angular housing 33 extending over an angle of at least 90° about the rotation axis XX. The first angular stop 29 and the second angular stop 31 form the angular extremities of an angular sector 32 consisting of a disc portion. The first coupling member 25 comprises a projecting element 35, in this example consisting of a pin. According to an embodiment not shown, the projecting element 35 is an angular sector consisting of a disc portion. The projecting element 35 is engaged in the angular housing 33 such that the second shaft 15 pivots freely about the rotation axis XX between a first angular position in which the projecting element 35 is in contact with the first angular stop 29 and a second angular position in which the projecting element 35 is in contact with the second angular stop 31.

The angular housing 33 extends over an angle of between 90° and 300° about the rotation axis, preferably equal to 295° as shown in this example.

In addition, the angle between the first angular position and the second angular position is at least 65°, preferably at least 90°, more preferably at least 180°, even more preferably at least 270°. In this example, this angle is 275°.

The detection means 19 detect the pivoting of the second shaft 15 out of the first angular position when the first shaft 9 is driven in rotation in a first direction of rotation S, and the pivoting of the second shaft 15 out of the second angular position when the first shaft 9 is driven in rotation in a second direction of rotation opposite to the first direction of rotation S.

The detection means 19 comprise a torque sensor 37 configured to measure the torque exerted by the electric motor 21 and/or a current sensor 39 configured to measure the current consumed by the electric motor 21. As an alternative or in addition, the detection means 19 comprise a first sensor 51 of the angular position of the first shaft 9 and a second sensor 53 of the angular position of the second shaft 15, which are for example included in the box 13. Preferably, the detection means 19 comprise a storage memory configured to store the angular position data of the first shaft 9 and of the second shaft 15.

The detection means 19 comprise a visual indicator of the switch from the first mode to the second mode. Preferably, the visual indicator of the switch from the first mode to the second mode comprises a green light emitting diode which is lit when the drive is carried out only according to the first mode, and comprises a red light emitting diode which is lit when the drive is carried out with at least a switch from the first mode to the second mode.

The detection means 19 comprise an audible indicator, which emits an audible signal when the drive is carried out only according to the first mode.

If the electric motor 21 makes a complete revolution and no decoupling occurred: activation is taken into account, the green light emitting diode comes on and the audible signal sounds. If the electric motor 21 makes a complete revolution and decoupling occurred, more precisely a switch from the first mode to the second mode: the red light emitting diode comes on. The angular position of the remote magnetic element 23 is for example determined as follows. Using the angular position of the second shaft 15, the angular position of the first shaft 9 and the torque of the electric motor 21, the angular position of the first shaft 9 driven by the electric motor 21 is determined during the switch to the second mode, and about 180 degrees, for example 181 degrees, must be subtracted from this angle to obtain the value of the angular position of the remote magnetic element 23.

The plate distractor 5 comprises a first attachment plate 41 and a second attachment plate 43, a distraction member 45 configured to modify the distance between the first attachment plate 41 and the second attachment plate 43, and the remote magnetic element 23 consisting of a permanent magnet.

The distraction member 45 comprises a threaded rod cooperating with a threaded hole in an attachment plate 41, 43 such as the first attachment plate 41, such that the thread pitch of the threaded rod is between 0.20 and 0.25 mm per revolution, preferably equal to 0.20 mm per revolution.

The remote magnetic element 23 is configured to drive the distraction member 45 in rotation about itself about a distraction axis YY, the remote magnetic element 23 being a permanent magnet magnetised along a direction Dd perpendicular to the distraction axis YY.

The distraction assembly 1 is such that, when the distraction axis YY coincides with the rotation axis XX: in the first mode, the remote magnetic element 23 is driven in rotation by the activation magnetic element 11, as shown on FIG. 3; in the second mode, the remote magnetic element 23 drives in rotation the activation magnetic element 11 until their magnetisation directions Da, Dd are parallel, more precisely parallel and opposite.

In the first mode shown on FIG. 3, the remote magnetic element 23 is driven in rotation in the first direction of rotation S by the activation magnetic element 11 by magnetic effect, due to the fact that their magnetisation directions Da, Dd are parallel, more precisely parallel and opposite. When the activation magnetic element 11 pivots, the remote magnetic element 23 pivots to keep their magnetisation directions Da, Dd parallel, more precisely parallel and opposite.

The switch to the second activation mode occurs when their magnetisation directions Da, Dd are no longer parallel, as shown in step 4*d* on FIG. 4, for example due to the fact that the rotation of the remote magnetic element 23 is blocked although the activation magnetic element 11 is driven in rotation.

FIG. 4, on views 4*a* to 4*f*, shows steps of the operation of the distraction assembly 1 when the remote magnetic element 23 is blocked in rotation, the first direction of rotation S of the first shaft 9 and of the projecting element 35 being shown on view 4*a*. In this case, when the activation magnetic element 11 is driven in rotation, the activation magnetic element 11 no longer drives in rotation the remote magnetic element 23.

On view 4*a*, the projecting element 35 is in contact with the first angular stop 29. At this stage, the magnetisation directions Da and Dd are parallel and opposite.

On view 4*b*, the projecting element 35 is still in contact with the first angular stop 29. At this stage, the magnetisation directions Da and Dd are no longer parallel. Nevertheless, the projecting element 35 still drives in rotation the second coupling member 27 via the first angular stop 29, which prevents the second coupling member 27, the second shaft 15 and the activation magnetic element 11 from pivoting in a second direction of rotation opposite to the first direction of rotation S to take up a position of equilibrium relative to the remote magnetic element 23, in which their magnetisation directions Da, Dd are parallel and opposite.

On view 4*c*, the projecting element 35 is still in contact with the first angular stop 29. At this stage, the magnetisation directions Da and Dd are parallel and in the same direction. Nevertheless, at this stage, the projecting element 35 still drives in rotation the second coupling member 27 via the first angular stop 29, which prevents the second coupling member 27 and the activation magnetic element 11 from taking up a position of equilibrium relative to the remote magnetic element 23.

On view 4*d*, the projecting element 35 is no longer in contact with the first angular stop 29. At this stage, the magnetisation directions Da and Dd are no longer parallel, the remote magnetic element 23 drives in rotation the activation magnetic element 11. Consequently, the second coupling member 27, the second shaft 15 and the activation magnetic element 11 pivot freely in the first direction of rotation S to take up an angular position of equilibrium relative to the remote magnetic element 23, in which their magnetisation directions Da, Dd are parallel and opposite, as shown on view 4*e*.

On view 4*f*, the second coupling member 27, the second shaft 15 and the activation magnetic element 11 are immobile in the angular position of equilibrium relative to the remote magnetic element 23, but the projecting element 35 has continued to pivot due to the drive via the first shaft 9 and the electric motor 21. In this case, since the first shaft 9 no longer drives the second shaft 15, the torque exerted by the motor is much lower than when the first shaft drives the second shaft 15. The projecting element 35 tends to move closer to the angular position occupied by the second coupling member, and finally comes back into contact with the first angular stop 29, as shown on view 4*a*.

When the first shaft 9 is driven in a second direction of rotation opposite to the first direction of rotation S, the operation is similar to that described above except that the first angular stop 29 is replaced by the second angular stop 31.

FIG. 5 is a diagrammatic representation of a distraction assembly according to a second embodiment, designated by the general reference 1'. The elements forming the distraction assembly 1' according to the second embodiment are similar to those forming the distraction assembly 1 according to the first embodiment, apart from the elements described below.

This distraction assembly 1' according to the second embodiment differs from the distraction assembly 1 according to the first embodiment mainly in that in the activation tool 3', a projecting element 35', similar to the projecting element 35 of the first embodiment, is supported by the second shaft 15, and in that an angular housing 33' is supported by the first shaft 9.

In this example, the first coupling member 25' comprises a first angular stop 29' and a second angular stop 31', the first angular stop 29' and the second angular stop 31' being angularly offset and delimiting between them the angular housing 33' extending over an angle of between 90° and 300°, preferably between 90° and 170°, and in this example equal to 135°. The first angular stop 29' and the second angular stop 31' form the angular extremities of an angular sector 32' consisting of a disc portion. The second coupling member 27' comprises a projecting element 35'. The projecting element 35' is engaged in the angular housing 33' such that the projecting element 35' pivots freely about the rotation axis XX between a first angular position in which the projecting element 35' is in contact with the first angular stop 29' and a second angular position in which the projecting element 35' is in contact with the second angular stop 31'.

In this embodiment, the detection means 19 comprise a first visual indicator 47 of the angular position of the first shaft 9 and a second visual indicator 49 of the angular position of the second shaft 15. In this example, the first visual indicator 47 consists of an arrow on the first coupling member 25', the arrow pointing towards the second coupling member 27'. The second visual indicator 49 consists of an arrow on the second coupling member 27', the arrow pointing towards the first coupling member 25'.

The operation of the distraction assembly 1' according to this second embodiment is similar to the operation of the distraction assembly 1 according to the first embodiment.

FIG. 6, on views 6*a* to 6*f*, shows steps of the operation of the distraction assembly 1' when the remote magnetic element 23 is blocked in rotation, the first direction of rotation S of the first shaft 9, of the angular sector 32' and of the angular stops 29' and 31' being shown on view 6*a*. In this case, when the activation magnetic element 11 is driven in rotation, the activation magnetic element 11 no longer drives in rotation the remote magnetic element 23.

However, since the angular housing 33' extends over an angle of between 90° and 170°, and in this example equal to 135°, when the first mode switches to the second mode, the projecting element 35' is no longer in contact with the first angular stop 29' in the first direction of rotation S, as shown on view 6*d* of FIG. 6. At this stage, the magnetisation directions Da and Dd are no longer parallel, the remote magnetic element 23 drives in rotation the activation magnetic element 11.

As shown on view 6*e* of FIG. 6, the projecting element 35' then comes into angular contact with the second angular stop 31'. For example, such a contact can be detected by a user, either because of the vibration due to this contact, or because of the sound generated by this contact. Thus, in this example, the detection means 19 also comprise the projecting element 35', the second angular stop 31' when the first shaft is driven in rotation in the first direction of rotation S, and the first angular stop 29' when the first shaft 9 is driven in a second direction of rotation opposite to the first direction of rotation S. During this contact, the second angular stop 31' provides a damping function due to the inertia in particular of the first shaft 9, until the second coupling member 27', the second shaft 15 and the activation magnetic element 11 take up an angular position of equilibrium relative to the remote magnetic element 23, in which their magnetisation directions Da, Dd are parallel and opposite, as shown on view 6*f* of FIG. 6. At this stage, the magnetisation directions Da and Dd are parallel, more precisely parallel and opposite, and neither the remote magnetic element 23 nor the first angular stop 29' drives 5 in rotation the activation magnetic element 11.

When the first shaft 9 is driven in a second direction of rotation opposite to the first direction of rotation S, the operation is similar to that described above except that the first angular stop 29' is replaced by the second angular stop 31', and vice versa.

The invention is not limited to the embodiments described and other embodiments will be clearly apparent to those skilled in the art. In particular, the embodiments can be combined together when this is technically feasible.

LIST OF REFERENCES

1, 1': distraction assembly
3, 3': activation tool
5: plate distractor
7: drive member
9: first shaft
11: activation magnetic element
13: box
15: second shaft
16: ball bearing
17: coupling device
19: detection means
21: electric motor 23: remote magnetic element
25, 25': first coupling member
27, 27': second coupling member
29, 29': first angular stop
31, 31': second angular stop
32, 32': angular sector
33, 33': angular housing
35, 35': projecting element
37: torque sensor
39: current sensor
41: first attachment plate
43: second attachment plate
45: distraction member
47: first visual indicator
49: second visual indicator
51: first sensor
53: second sensor
XX: rotation axis
YY: distraction axis
Da: magnetisation direction of the activation magnetic element
Dd: magnetisation direction of the remote magnetic element
S: first direction of rotation

The invention claimed is:

1. Activation tool (3, 3') for a bone expansion apparatus, preferably for a plate distractor (5), the activation tool (3, 3') comprising:
   a drive member (7) provided with a drive output,
   a first shaft (9) configured to be driven in rotation about a rotation axis via the drive output,
   an activation magnetic element (11) configured to interact, preferably coaxially, with a remote magnetic element (23) supported by the bone expansion apparatus,
   a second shaft (15), arranged coaxially to the first shaft (9), the second shaft (15) supporting the activation magnetic element (11),
   a coupling device (17) interposed between the first shaft (9) and the second shaft (15), which is configured to couple the first shaft (9) and the second shaft (15) in a first mode, referred to as the activation mode, when the first shaft (9) and the second shaft (15) exhibit the same rotational speed, and is configured to angularly decouple the first shaft (9) and the second shaft (15) in a second mode, referred to as the failure mode, when a rotational speed of the second shaft (15) is higher than the rotational speed of the first shaft (9), and
   means (19) for detecting the switch from the first mode to the second mode,
   the coupling device (17) comprising:
   a first coupling member (25, 25') supported by the first shaft (9), and
   a second coupling member (27, 27') supported by the second shaft (15),
   one selected from the first coupling member (25, 25') and the second coupling member (27, 27') comprising a first angular stop (29, 29') and a second angular stop (31, 31'), the first angular stop (29, 29') and the second angular stop (31, 31') being angularly offset and delimiting between them an angular housing (33, 33') extending over an angle of at least 90° about the rotation axis, the other selected from the first coupling member (25, 25') and the second coupling member (27, 27') comprising a projecting element (35, 35'),
   the projecting element (35, 35') being engaged in the angular housing (33, 33') such that the second shaft (15) pivots freely about the rotation axis (XX) between a first angular position in which the projecting element (35, 35') is in contact with the first angular stop (29, 29') and a second angular position in which the projecting element (35, 35') is in contact with the second angular stop (31, 31').

2. Activation tool (3, 3') according to claim 1, wherein the projecting element (35, 35') is a pin or an angular sector consisting of a disc portion, and wherein the first angular stop (29, 29') and the second angular stop (31, 31') form the angular extremities of an angular sector consisting of a disc portion.

3. Activation tool (3, 3') according to claim 2, wherein the angular housing (33, 33') extends over an angle of between 90° and 300° about the rotation axis (XX).

4. Activation tool (3, 3') according to any claim 1, wherein the drive member (7) comprises an electric motor (21).

5. Activation tool (3, 3') according to claim 1, wherein the means (19) for detecting comprise a first sensor (51) of the angular position of the first shaft (9) and a second sensor (53) of the angular position of the second shaft (15).

6. Activation tool (3, 3') according to claim 4, wherein the means (19) for detecting comprise a torque sensor (37) configured to measure the torque exerted by the electric motor (21) and/or a current sensor (39) configured to measure the current consumed by the electric motor (21).

7. Activation tool (3, 3') according to claim 1, wherein the rotational speed of the activation magnetic element (11) in the first mode is less than or equal to 30 revolutions per minute, preferably less than or equal to 18 revolutions per minute.

8. Activation tool (3, 3') according to claim 1, which comprises a ball bearing (16) arranged on the second shaft (15).

9. Distraction assembly (1, 1') comprising:
   an activation tool (3, 3') according to claim 1, wherein the activation magnetic element (11) is a permanent magnet magnetised along a direction (Da) perpendicular to the rotation axis (XX), and
   a plate distractor (5), which comprises a first attachment plate (41), a second attachment plate (43), a distraction member (45) configured to modify the distance between the first attachment plate (41) and the second attachment plate (43), and a remote magnetic element (23) consisting of a permanent magnet, configured to drive the distraction member (45) in rotation about itself about a distraction axis (YY), the remote magnetic element (23) being a permanent magnet magnetised along a direction (Dd) perpendicular to the distraction axis (YY).

10. Activation tool (3, 3') according to claim 1, wherein the angular housing (33, 33') extends over an angle of between 90° and 300° about the rotation axis (XX).

* * * * *